(12) United States Patent
Gaines et al.

(10) Patent No.: US 8,235,308 B2
(45) Date of Patent: Aug. 7, 2012

(54) FRAGRANCE DISPENSING ASSEMBLY WITH BUOYANT REEDS

(75) Inventors: Kelly Gaines, Sugar Land, TX (US); Andrea Garrison, Houston, TX (US)

(73) Assignee: Gaines Group LLC, Houston, TX (US)

( * ) Notice: Subject to any disclaimer, the term of this patent is extended or adjusted under 35 U.S.C. 154(b) by 180 days.

(21) Appl. No.: 12/254,559

(22) Filed: Oct. 20, 2008

(65) Prior Publication Data

US 2009/0039174 A1  Feb. 12, 2009

Related U.S. Application Data

(63) Continuation-in-part of application No. 11/818,412, filed on Jun. 14, 2007.

(60) Provisional application No. 60/884,977, filed on Jan. 15, 2007.

(51) Int. Cl.
*B65D 69/00* (2006.01)
*A24F 25/00* (2006.01)
*A61L 9/04* (2006.01)

(52) U.S. Cl. .......................................... 239/44; 206/229

(58) Field of Classification Search .................. 206/223, 206/229, 443, 576, 581, 823; 239/44, 57, 239/145, 33
See application file for complete search history.

(56) References Cited

U.S. PATENT DOCUMENTS

| | | | | |
|---|---|---|---|---|
| 1,253,579 A * | 1/1918 | Deanes | ........................ | 215/11.1 |
| 1,839,073 A * | 12/1931 | Wright | ............................ | 239/50 |
| 4,019,856 A * | 4/1977 | Lacroix | .......................... | 431/298 |
| 4,419,326 A * | 12/1983 | Santini | ............................... | 422/4 |
| 4,915,301 A * | 4/1990 | Munteanu | ........................ | 239/45 |
| 5,160,058 A * | 11/1992 | Ahn | ............................... | 215/388 |
| 5,651,942 A | 7/1997 | Christensen | | |
| 5,840,246 A | 11/1998 | Hammons et al. | | |
| 5,848,721 A * | 12/1998 | Cornell et al. | ................. | 220/706 |
| 5,908,231 A | 6/1999 | Huff | | |
| 6,230,913 B1 * | 5/2001 | Cornell et al. | ................. | 215/387 |
| 6,244,501 B1 | 6/2001 | Choi | | |
| 6,372,313 B1 | 4/2002 | D'Alessio et al. | | |
| 6,381,901 B1 | 5/2002 | Friedman | | |
| 6,508,373 B1 | 1/2003 | Robinson | | |
| 6,548,015 B1 | 4/2003 | Stubbs et al. | | |
| 6,568,529 B2 | 5/2003 | McMurrey | | |
| 6,785,467 B2 | 8/2004 | White et al. | | |
| 6,802,416 B1 | 10/2004 | D'Alessio et al. | | |
| 6,921,024 B2 | 7/2005 | Donnelly et al. | | |

(Continued)

OTHER PUBLICATIONS

"Aroma Sticks Ceramic Fragrance Diffuser" product instructions; 1 page; undated.

(Continued)

*Primary Examiner* — Mickey Yu
*Assistant Examiner* — Rafael Ortiz
(74) *Attorney, Agent, or Firm* — Douglas W. Rommelmann; Andrews Kurth LLP

(57) ABSTRACT

A fragrance dispensing assembly including a container having a sealed interior chamber containing porous reeds in a fragranced liquid. At least one buoyant member is coupled to one or more of the reeds. The porous reeds, buoyant member(s) and the fragranced liquid are put in the container and placed in contact with each other prior to sealing the container. To commence use of the fragrance dispensing assembly, the sealed container is opened and the buoyant member(s) elevate the coupled porous reeds within the liquid, thus providing additional portions of the pre-soaked porous reeds to extend from the opened container and begin instant and continuous fragrance dispensing to a room upon opening the sealed container.

18 Claims, 2 Drawing Sheets

U.S. PATENT DOCUMENTS

| | | |
|---|---|---|
| 6,960,040 B2 | 11/2005 | D'Alessio et al. |
| 6,969,008 B2 | 11/2005 | Helf et al. |
| 7,025,229 B2 | 4/2006 | Bochno et al. |
| D605,746 S * | 12/2009 | Butler et al. ............ D23/366 |
| 2001/0002532 A1* | 6/2001 | Murphy et al. ............ 53/445 |
| 2003/0208175 A1* | 11/2003 | Gross et al. ............ 604/378 |
| 2007/0158454 A1* | 7/2007 | Ching-Chong ............ 239/33 |
| 2008/0169220 A1* | 7/2008 | Gaines ............ 206/576 |
| 2008/0217425 A1* | 9/2008 | Butler et al. ............ 239/45 |
| 2008/0308648 A1* | 12/2008 | Pesu ............ 239/44 |

OTHER PUBLICATIONS

Pier 1 Imports; SKU 2145818 product instructions; 1 page; undated.
Pier 1 Imports; SKU 2137930 product instructions; 1 page; undated.

* cited by examiner

FRAGRANCE DISPENSING ASSEMBLY WITH BUOYANT REEDS

CROSS-REFERENCE TO RELATED APPLICATIONS

This application is a continuation-in-part of U.S. patent application Ser. No. 11/818,412, filed Jun. 14, 2007, which claims priority from U.S. provisional application Ser. No. 60/884,977, filed Jan. 15, 2007. Applicant incorporates by reference herein U.S. patent application Ser. No. 11/818,412 and U.S. Provisional Application Ser. No. 60/884,977 in their entirety.

BACKGROUND OF THE INVENTION

1. Field of the Invention

The present invention relates to fragrance dispensing assemblies, and more particularly relates to devices and techniques for dispensing fragrance instantly and continuously into a surrounding area and a method of packaging same.

2. Description of the Related Art

Various techniques exist for releasing fragrance into the air. These techniques are often used in homes, offices, or other enclosed areas in order to eliminate unpleasant odors or simply to add a pleasing fragrance into the air. Burning scented candles, for example, release fragrance from the melted wax but can be hazardous if left unattended. Furthermore, office buildings and other public places prohibit burning candles due to safety and/or fire code regulations.

Another technique used to emit a fragrant scent in the air is with the use of potpourri. Traditional potpourri comprises various mixtures of aromatic herbs, dried flowers, and spices blended with essential oils. The potpourri is usually contained within a bowl or a basket so that it can release its fragrance into the air. Typically, the potpourri scent is emitted in a very confined space and lasts only a short period of time. Within a day or two, the potpourri mixture is dried up and ready to be discarded. Fragrant oils can be sprayed or dripped onto the potpourri to enhance the aroma, but again the area in which this is effective is very small.

Another technique is to use the potpourri with an external heat source and water to cause the fragrance to become airborne through the vaporization process of boiling the water. The potpourri mixture is typically placed in a pot of water which is then heated. Although this technique is effective in making the aroma stronger and more widely spread, it has disadvantages. The disadvantages are that the heat source is typically either an electrical heating element or an open flame (such as a burning candle), both of which can be dangerous. Additionally, if the heated water is touched or spilled, it could burn badly, and, if all of the water in the pot is vaporized and the heat source remains on, the potpourri material itself can be set on fire.

Still another technique has been developed and used the last few years. This technique involves the use of slender reeds, typically made of wood, and fragranced liquid or oil placed in an open container or bottle. With the fragranced liquid in the container, one end of the reeds are inserted through the opening of the container into the fragranced liquid and a second end of the reeds extend above the container opening. The reeds each have a length such that when the first end comes to rest inside the container, the second end extends into the space above the container opening. The first end of the reeds are in the fragranced liquid in the container. The hygroscopic nature of the reed material allows the reeds to absorb the fragranced liquid in the hollow space between the walls of the wood cells. After a period of time, the fragranced liquid is drawn or absorbed to the upper ends of the reeds resulting in fragranced liquid evaporating and being diffused into the surrounding area.

The fragrant reed technique has the advantages of no open flame or heat source required to scent the air, it scents the air continuously and can be left unattended. However, this technique has the disadvantage of requiring a lengthy period of time before it begins to diffuse the scent into the room. This is due to the amount of time required for the reeds to absorb the fragranced liquid throughout the length of the reeds. For example, various commercially available fragrant reed products indicate that, for reeds having a length of approximately 10", the reeds will draw and diffuse the fragrance within approximately 36 to 48 hours. The fragrant reeds will then continue to diffuse the fragrance throughout the room for extended periods of time depending on the amount of fragranced liquid and number of reeds being used. For example, 10 reeds and 6 ounces of fragranced liquid will typically continue to scent an area for several weeks.

To further enhance and/or refresh the fragrance dispensing ability of the diffusing items (i.e., the reeds), current retail products recommend periodically flipping the reeds by removing the reeds from the container and inserting the second end of the reeds into the fragranced liquid in the container. This results in the "new" second end of the reeds (i.e., the portion extending out of the container opening) having a fragrance liquid film on the outer surface area of the reed portions which provides enhanced diffusing of the fragrance until such time the liquid film on the exposed outer surface of the reeds evaporates.

The above "flipping" process is messy and inconvenient for the end user. The fragrance liquid, typically an oil, may contact the consumer's skin and/or the furniture the container rests on. As a result, consumers are unlikely to repeat this process and may become disenchanted with the product and/ or conclude the product does not work without the aggravations associated with the flipping process.

It would be desirable to provide a fragrance dispensing assembly and method which requires no open flame or heat source and which scents the air continuously and can be left unattended. It would also be desirable to provide a fragrance dispensing assembly and technique that dispenses a fragrance throughout a room immediately without the extended waiting period currently required with commercially available dry reeds. Additionally, it would be desirable to have a fragrance dispensing assembly with reeds that provides all the advantages of existing reed products but with enhanced fragrance dispensing ability without the inconveniences of existing products.

SUMMARY OF THE INVENTION

The preferred embodiment of the present invention is a technique and assembly for providing a fragrance dispensing device requiring no open flame or heat source and which scents a room immediately and continuously and can be left unattended. The preferred embodiment of the invention provides a fragrance dispensing assembly and technique that dispenses a fragrance throughout a room immediately without the extended waiting period currently required when placing dry reeds into a container holding fragranced liquid. The preferred embodiment of the present invention also allows a method for enhancing the fragrance dispensing ability of the reeds without the mess and inconveniences of existing similar products.

BRIEF DESCRIPTION OF THE DRAWINGS

A better understanding of the present invention can be obtained when the following detailed description of preferred embodiments is considered in conjunction with the drawings in which.

DETAILED DESCRIPTION OF PREFERRED EMBODIMENTS

Figure 2:
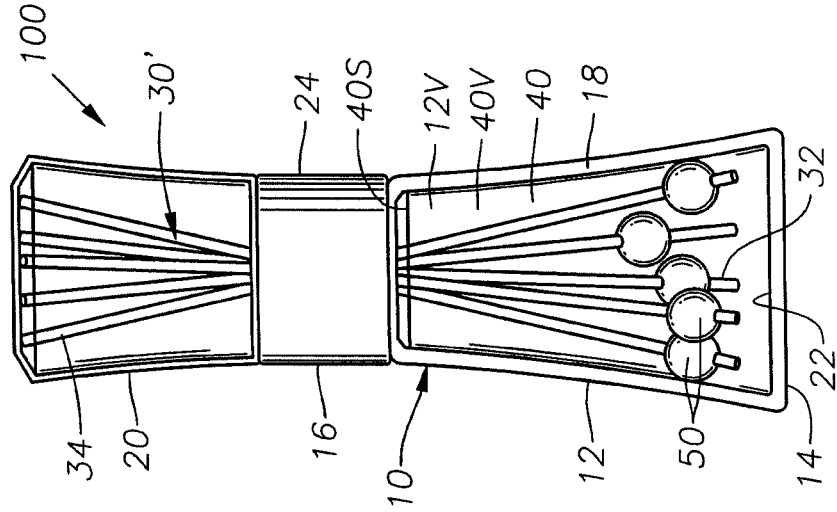
FIG. 2 is an elevation view of the preferred embodiment of the present invention shown in FIG. 1.
Figure 1:
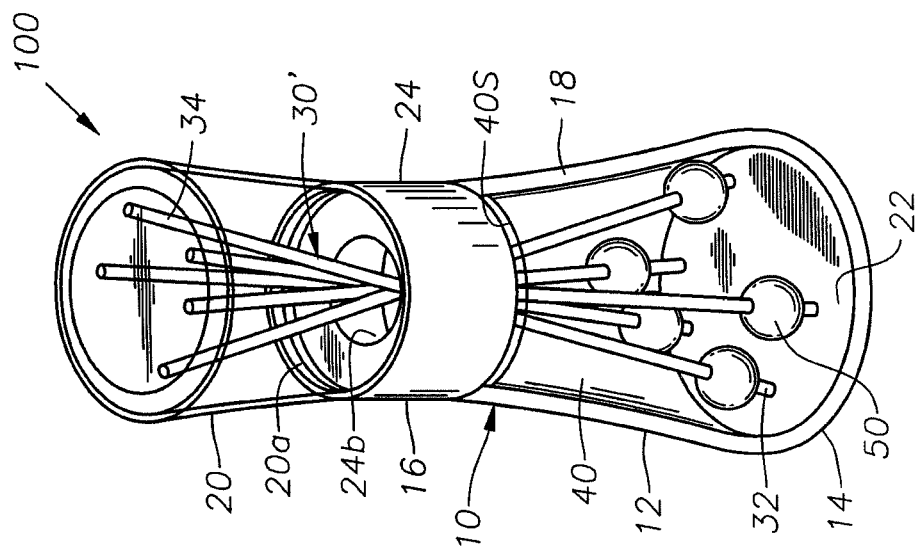
FIG. 1 is a perspective view of a preferred embodiment of the present invention having a plurality of reeds and fragranced liquid packaged in a container, the container illustrated in a closed condition with a removable cap at the upper end of the container.

With reference to the drawings, the preferred embodiments of the present invention will now be described in detail. Referring to FIGS. 1 and 2, a fragrance dispensing assembly 100 according to a preferred embodiment includes a container 10 having a base portion 12 and a cap 20. The cap 20 is preferably removably attached to the base portion 12, and more preferably threadably attached to the base portion 12. Preferably, the base portion 12 includes lower and upper ends, 14 and 16 respectively, joined by a container wall 18. The wall 18 is joined to a base member 22 at the lower end 14 and to a collar 24 at the upper end 16. It is to be understood that the base portion 12 may be of unitary construction, as for example by molding or forming processes, or may be assembled from two or more components. It is to be understood that the container 10 defines a fluid-tight enclosure when the cap 20 is secured to the base portion 12.

As shown in FIG. 1, the container 10 is preferably adapted to be positioned upright with the cap 20 positioned above the base portion 12. Preferably, the lower end 14 is adapted to provide stability when the container 10 is stood upright on the base member 22, especially when the cap 20 is removed during use of the fragrance dispensing assembly 100.

Figure 5:
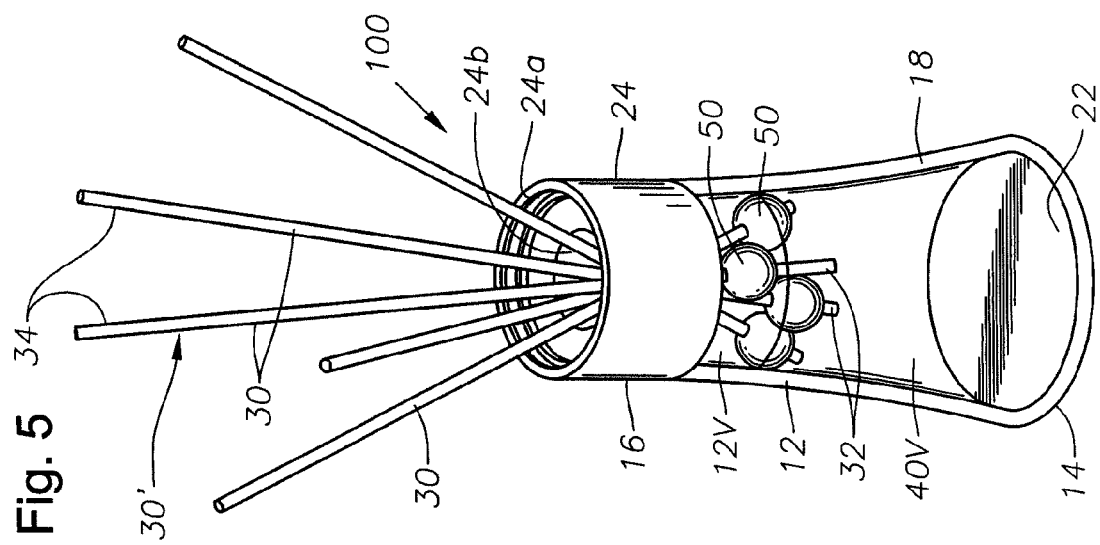
FIG. 5 is a perspective view of the preferred embodiment of the present invention shown in FIG. 1 with the cap removed and the reeds floating in the fragrance liquid.
Figure 4:
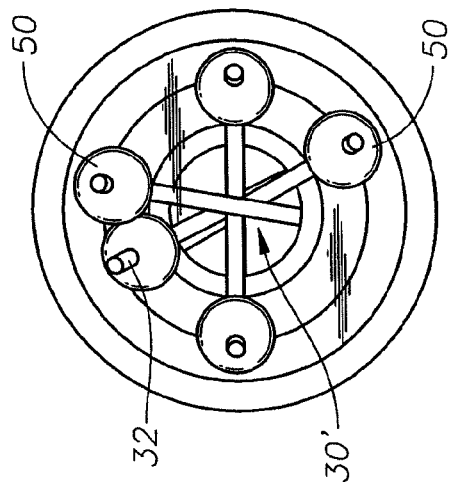
FIG. 4 is a bottom view of the preferred embodiment of the present invention shown in FIG. 1.

With reference to FIGS. 1 and 5, the collar 24 at the upper end 16 of the base portion 12 preferably includes an internally threaded segment 24a adapted to engage an externally threaded segment 20a of the cap 20. As stated above, the cap 20 preferably provides a fluid-tight seal with the base portion 12 of the container 10 when secured thereto.

Figure 3:
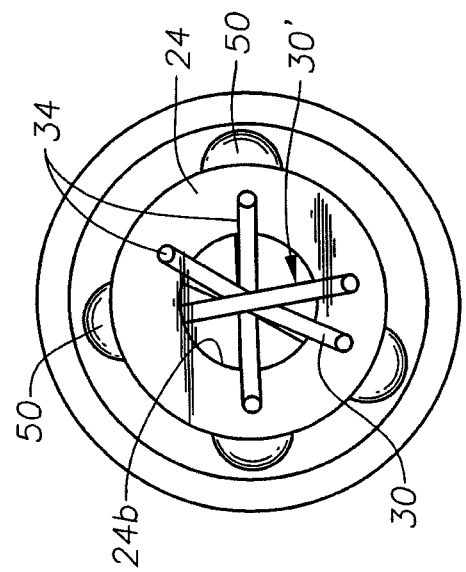
FIG. 3 is a top view of the preferred embodiment of the present invention shown in FIG. 1.

Referring to FIGS. 1, 3 and 5, the collar 24 includes an aperture 24b extending therethrough. The aperture 24b provides an opening for a plurality of diffusing items 30, preferably reeds, to extend through. It is to be understood that the collar 24 and aperture 24b can be integrally formed with the container wall 18 or the collar 24 can be a separate component that is securely attached or joined to the container wall 18.

Preferably, the plurality of reeds 30 are placed in the container 10. Each reed is preferably elongate and slender having a first end 32 and a second end 34. The reeds 30 are preferably made of a porous, wicking material, as for example wood rattan. Each reed has a length defined by the distance between the first and second ends 32 and 34, respectively. Preferably, the reeds 30 forming the plurality of reeds all have approximately the same length. Common reed lengths range from 6" to 15", although it is to be understood that the present invention is not limited to these lengths. In the preferred embodiment of the present invention, the reeds have a length which allows the plurality of reeds to be within the sealed container 10 when the cap 20 is attached to the base portion 12.

According to a preferred embodiment of the present invention, a buoyant member 50 or members are coupled to one or more of the reeds 30 for reasons which will be explained below. As used herein, buoyant member is a member that tends to float or rise when submerged in liquid, such as the fragranced liquid 40. In the preferred embodiment shown in the figures, the buoyant members 50 comprise a generally spherical member through which the reed 30 extends. Preferably, the lower first end 32 of the reeds 30 are exposed to the fragranced liquid 40 within the base portion 12 so that the hygroscopic nature of the reed material allows the reeds to absorb the fragranced liquid in the hollow space between the walls of the wood cells. It is to be understood that the buoyant members 50 can take on a variety of shapes and sizes, and be made of a variety of materials, and can be coupled to the reeds in a variety of ways. Merely by way of example, the buoyant member 50 may be made from glass, wood, metal, or plastics, including but not limited to polyurethane and polystyrene plastics. The construction of the buoyant member 50 may depend on the type of material that it is made from. For example, a wooden buoyant member 50 will likely be comprised of a solid member having a hole drilled through it whereas a glass buoyant member 50 may be formed as a generally sealed hollow sphere having a "walled" bore extending through the member to prevent liquid from filling the buoyant member 50. It is to be understood that the construction of the buoyant member 50 will to some extent depend on the material type and its buoyancy. Although not shown, it is also to be understood that a single buoyant member 50 may be used to simultaneously float a plurality of reeds 30 as opposed to floating merely a single reed 30.

Figure 7:
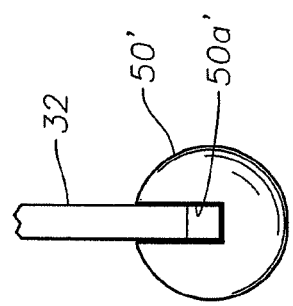
FIG. 7 is an alternative embodiment of a buoyant member.

FIG. 7 shows one form of alternate embodiment for the buoyant member referred to as 50'. In this embodiment, the buoyant member 50' includes a bore 50a' that preferably terminates within the buoyant member 50'. For example, the bore 50a' may be a "blind" bore. Preferably, the bore 50a' is sized and shaped to frictionally engage the lower end 32 of the reed 30 while also permitting fragranced liquid to enter and fill the lower portion of the blind bore 50a' (adjacent to the porous end of the reed) when coupled to the reed 30. In this particular embodiment, the buoyant member 50' is preferably designed such that the buoyant member 50' remains at least slightly submerged in the liquid 40 during use to allow the liquid to constantly enter the blind bore 50a', thus allowing the lower end of the reed 30 to continue to wick. It is to be understood that alternatively the buoyant member 50' may be made of a buoyant material that is porous and/or has a wicking nature such that the liquid will come into contact with the lower end of the reed 30 even if the buoyant member 50' is not totally submerged. Still another alternative is to include an additional passageway in the buoyant member 50' for continuously providing the fluid to the porous end of the reed.

The base portion 12 of the container 10 has an interior volume 12V generally defined as the space between the collar 24 and the base member 22 within the peripheral container wall 18. The plurality of reeds 30 with buoyant members 50 (hereinafter jointly referred to as buoyant reeds 30') and a volume 40V of fragranced liquid 40 are placed in the interior volume 10V of the base portion 12 of the container 10. Preferably, the plurality of reeds 30 are initially "dry" (i.e, not saturated with fragranced liquid) upon placement into the base portion 12. In the preferred embodiment, the buoyant reeds 30' are inserted into the base portion 12 via the collar aperture 24a. However, it is to be understood that if the collar 24 is removable from the container wall 18 (as for example, via a threaded connection (not shown)), the buoyant reeds 30' may be inserted into the base portion 12 and then the upper second end 34 of the reeds 30 are passed through the collar aperture 24a prior to securing the collar 24 to the container wall 18. The fragranced liquid 40 may be similarly placed in the base portion 12, preferably either prior to or after inserting the buoyant reeds 30'.

Figure 6:
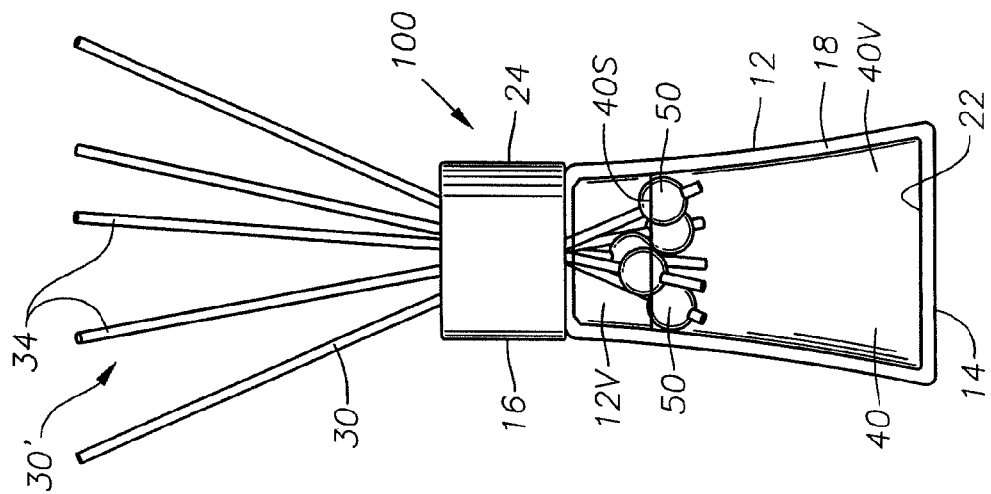
FIG. 6 is an elevation view of the preferred embodiment shown in FIG. 5.

Following insertion of the buoyant reeds 30' and fragranced liquid 40 in the base portion 12, the dispensing assembly 100 may have the general appearance as shown in FIGS. 5 and 6. As shown in FIGS. 5 and 6, the buoyant members 50 rise toward the upper surface 40S of the fragranced liquid 40. Preferably, the buoyant members 50 are coupled to the reeds 30 so as to substantially retain their point of attachment and prevent relative movement between them during normal use of the fragrance dispensing assembly 100. For example, a friction fit between the buoyant member 50 and the reed 30 which maintains the buoyant member 50 at the same point on the reed 30 during normal use of the fragrance dispensing assembly 100 is desirable. It is to be understood that the buoyant members 50 may be positioned at different points along the length of the various reeds 30 to provide different aesthetic or ornamental effects.

In the preferred embodiment, the dry upper end 34 of the buoyant reeds 30' are brought closely together to allow the cap 20 to be secured to the base portion 12 as shown in FIGS. 1 and 2. The cap 20 is preferably sealingly engaged to the upper end 16 of the base portion 12 to define a sealed interior chamber within the container 10. Once sealed, the packaged assembly of the plurality of buoyant reeds 30', the volume 40V of fragranced liquid 40 and the container 10 are packaged and ready to ship or distribute to retail outlets, distributors, and end users.

As shown in FIGS. 1 and 2, the lower end 32 of the reeds 30 are preferably exposed to the fragranced liquid 40 and the lower portion of the reeds 30 are immersed in the fragranced liquid 40 within the base portion 12 of the container 10. Preferably, at least half of the reed length is immersed in the fragranced liquid 40 upon packaging the fragrance dispensing assembly 100.

It is to be understood that the plurality of reeds 30 commence drawing, absorbing, wicking and/or becoming saturated with the fragranced liquid 40 upon being packaged. The hygroscopic nature or the porous, wicking nature of the reeds 30 will draw up the fragranced liquid 40 to the second end 34 of the reeds 30 if shipped, stored or displayed in the upright orientation as shown in FIGS. 1 and 2. However, if the container 10 is inverted from that shown in FIGS. 1 and 2, the fragranced liquid 40 will fill the cap 20 and the second end 34 of the reeds 30 will be exposed and immersed in the fragrant fluid 40 to allow the wicking and absorbing action described above. Similarly, if the container 10 is oriented on its side, the fragranced liquid 40 will still remain in contact with at least a substantial portion of the reeds 30 and one of the reed ends 32 or 34.

The use of the preferred embodiment of the fragrance dispensing assembly 100 will now be described. Preferably, the sealed container 10 is inverted to allow the fragranced liquid 40 to fill the interior of the cap 20 and form a liquid film on the external surface of the entire length of the reeds 30. The container 10 is then brought to the upright position as shown in FIGS. 1 and 2. Preferably, after allowing the excess fragranced liquid 40 to drain from the cap into the base portion 12, the cap 20 is removed. In the preferred embodiment, the internally threaded collar 24 helps to retain the liquid 40 in the base portion 12 as the cap 20 is removed in addition to providing a more pleasing appearance of the base portion 12 during use. As the cap 20 is removed, the buoyant members 50 rise toward the liquid surface 40S in the base portion 12 as shown in FIGS. 5 and 6. As the buoyant members 50 rise in the fragranced liquid 40, the coupled reeds 30 also rise through the collar aperture 24b into the space above the base portion 12.

It is to be understood that upon removing the cap 20, the pre-soaked and saturated reeds 30 immediately diffuse fragrance into a room or the surrounding area for ultimate fragrance enjoyment—without any lengthy delay. It is also to be understood that the instant fragrance diffusion is enhanced by the fragranced liquid 40 present on the exposed exterior surface of the reeds 30 outside of the base portion 12 of the container 10.

Preferably, the buoyant member 50 is coupled to the reed 30 proximate or near the lower first end 32 of the reeds 30. This results in a greater length of the reeds 30 extending outside of the base portion 12, thus exposing a greater amount of liquid film coated external surface area of the reeds 30 providing even greater enhanced dispensing of the fragrance by the dispensing assembly 100.

After using the preferred embodiment of the fragrance dispensing assembly 100 for a period of time such that the exposed external surface of the reeds 30 is relatively dry to the touch, the fragrance dispensing of the assembly 100 may be refreshed or enhanced by bringing the exposed upper portion of the reeds 30 together and securing the cap 20 to the base portion 12. With the cap 20 firmly secured, the container 10 is inverted to allow fragranced liquid 40 in the base portion 12 to travel along the length of the reeds 30 and coat the exterior surface of the reeds 30 with a liquid film, and/or pass through the collar aperture 24b into the cap 20 and coat the reed portions immersed in the liquid 40 when in the inverted condition. The container 10 is then brought back to its upright position as shown in FIGS. 1 and 2, and, after allowing the excess fragranced liquid 40 to drain from the cap into the base portion 12, the cap 20 is again removed and the fragrance dispensing assembly 100 operates as described above.

The preferred embodiment of the fragrance dispensing assembly 100 provides several advantages:
  (1) it is simple to use—just remove the cap;
  (2) no mess to initially begin use—there is no transferring the fragranced liquid from one container to another in order to use;
  (3) no wait; instantly gratifying—the pre-soaked diffusing items packaged in the fragranced liquid provides instant fragrance dispensing upon removal of the cap (in contrast to dry reeds that can take 36 to 48 hours before omitting the fragrance);
  (4) enhanced fragrance dispensing—
    (a) buoyant members provide greater "reach" by the exposed reed ends;
    (b) buoyant members provide greater exposed surface area of the reeds outside of the container;
  (5) no mess/no spill when enhancing/refreshing the fragrance dispensing ability of the assembly—simply re-install and tighten the cap to the base portion of the liquid container, invert the container to permit moistening of the exterior surface of the reeds, when complete bring the container back to its original position and allow any excess liquid to drain out of the cap and back into the container base portion; remove the cap and the procedure is finished;

(6) the unique technique for elevating the diffusing items within the container when the cap is removed creates a self-contained vase that can be used for the duration of the product's life; and (7) "oil" level indicator—the height of the diffusing items provides a visual indicator to the consumer of the amount of liquid remaining in the container. As the liquid is diffused, the liquid level and the height of the reeds decreases. This change in reed height with time provides the consumer with a visual reminder as to when it is time to replace the fragrance dispensing assembly.

It is to be understood that the base portion 12 according to the preferred embodiment of the present invention may be transparent to allow the liquid 40, buoyant members 50, 50' and reeds 30 to be seen during normal use of the fragrance dispensing assembly 100.

The foregoing disclosure and description of the invention are illustrative and explanatory thereof, and various changes in the size, shape and materials, as well as the details of the illustrated operation and construction may be made without departing from the spirit and scope of the invention.

We claim:

1. A packaged kit for storing an instant fragrance dispensing assembly comprising:
    a container defining a sealed interior chamber;
    a plurality of diffusing items within said sealed interior chamber, said plurality of diffusing items made of a material selected for its wicking nature;
    a buoyant member within said sealed interior chamber and attached to at least one of said plurality of diffusing items; and
    a fragranced liquid within said sealed interior chamber, said fragranced liquid contacting said buoyant member and at least one of said plurality of diffusing items;
    wherein said buoyant member and attached said at least one diffusing item are buoyant in said fragranced liquid in said sealed interior chamber.

2. The packaged kit of claim 1, wherein said fragranced liquid contacts each of said plurality of diffusing items in said sealed interior chamber.

3. The packaged kit of claim 1, wherein said diffusing items are elongate.

4. The packaged kit of claim 1, wherein said diffusing items are wooden.

5. The packaged kit of claim 1, wherein said fragranced liquid contacts a porous end of each of said plurality of diffusing items in said sealed interior chamber.

6. The packaged kit of claim 2, wherein said container includes a replaceable cap.

7. A method of packaging a fragrance dispensing assembly, the method comprising the steps of:
    providing a container having a base portion and a removable cap;
    providing a plurality of diffusing reeds made of a material selected for its wicking nature;
    inserting a volume of fragranced liquid in the container;
    attaching a buoyant member to at least one of the plurality of diffusing reeds;
    inserting the plurality of diffusing reeds in the container;
    placing the plurality of diffusing reeds and buoyant member in contact with the volume of fragranced liquid such that the buoyant member provides buoyancy to the buoyant member and the attached at least one of the plurality of diffusing reeds in the fragranced liquid; and
    sealing the container.

8. A fragrance dispensing assembly comprising:
    a container including a cap and a base portion, said base portion having an aperture and defining an interior volume;
    a plurality of diffusing items in said container, said plurality of diffusing items made of a material selected for its hygroscopic nature;
    a buoyant member attached to at least one of said plurality of diffusing items;
    a fragranced liquid within said container contacting said plurality of diffusing items,
    wherein the assembly includes a first arrangement and a second arrangement, in said first arrangement said cap and said base portion define a sealed interior chamber of said container and said plurality of diffusing items, said buoyant member and said fragranced liquid are contained within said sealed interior chamber,
    wherein in said second arrangement, said buoyant member elevates said attached diffusing item upon removal of said cap from said base portion.

9. The fragrance dispensing assembly of claim 8, wherein said base portion has a height and at least one of said plurality of diffusing items has a length greater than said base portion height such that said at least one diffusing item protrudes from said interior volume through said aperture of said base portion into a space within said cap in said first arrangement.

10. The fragrance dispensing assembly of claim 8, further comprising a plurality of buoyant members, wherein each said diffusing item has attached at least one said buoyant member.

11. The packaged kit of claim 1, wherein said container comprises a base portion and a cap, said base portion having a base height and at least one of said diffusing items having a straight portion defining a length that is greater than said base height.

12. The packaged kit of claim 1, further comprising a plurality of buoyant members, wherein each said diffusing item has attached at least one said buoyant member.

13. The method of claim 7, wherein each of said plurality of diffusing reeds is wooden.

14. A method of using a fragrance dispensing assembly including a container containing a fragranced liquid, a plurality of diffusing reeds made of a material selected for its wicking nature, and a buoyant member coupled to at least one diffusing reed and contacting the fragrance liquid; the container including a base portion and a cap, the method comprising the steps of: sealing the container by placing the cap on the base portion with the plurality of diffusing reeds and fragranced liquid within the container; bringing the fragranced liquid into contact with the entire external surface area of the plurality of diffusing reeds while the container is sealed; and removing the cap and positioning the container upright on its base portion with a portion of each of the diffusing reeds extending above the base portion.

15. The method of claim 14, wherein said step of bringing the fragranced liquid into contact with the entire external surface area of the plurality of diffusing reeds comprises inverting the sealed container.

16. A fragrance dispensing assembly comprising:
    a container including a cap and a base portion, said base portion having an aperture and defining an interior volume;
    a plurality of buoyant diffusing item assemblies in said container each said buoyant diffusing item assembly comprising a diffusing item made of a material selected for its hygroscopic nature and a buoyant member coupled to said diffusing item; and a fragranced liquid within said container contacting said plurality of buoyant diffusing item assemblies, wherein the fragrance dispensing assembly includes a first arrangement and a second arrangement, in said first arrangement said cap and said base portion define a sealed interior chamber of said container and said plurality of buoyant diffusing item assemblies and said fragranced liquid are entirely contained within said sealed interior chamber, wherein in said second arrangement, each said buoyant member elevates said coupled diffusing item upon removal of said cap from said base portion.

17. The fragrance dispensing assembly of claim 16, wherein said container base portion has a height and each of said buoyant diffusing item assemblies has a length and said base portion height is less than the length of each said buoyant diffusing item assembly.

18. The fragrance dispensing assembly of claim 16, wherein each said diffusing item has a first end and a second end defining a diffusing item length, each said diffusing item being elongate and slender and having a stiffness maintaining said first end a distance of substantially said diffusing item length from said second end.

* * * * *